United States Patent
Tokarz

Patent Number: 5,368,638
Date of Patent: Nov. 29, 1994

[54] NATURAL EAR PLUG COMPOSITION

[76] Inventor: Joseph F. Tokarz, 211 Van Ness Ave., Ashland, Oreg. 97520

[21] Appl. No.: 82,104

[22] Filed: Jun. 28, 1993

[51] Int. Cl.$^5$ ............................................... C08L 3/06
[52] U.S. Cl. .................................. 106/212; 128/864; 514/778
[58] Field of Search .............. 106/212; 128/864; 514/778

[56] References Cited

U.S. PATENT DOCUMENTS

| | | | |
|---|---|---|---|
| 2,574,288 | 11/1951 | Rosenblatt | 128/864 |
| 3,852,475 | 12/1974 | Tarangul | 514/778 |
| 3,928,666 | 12/1975 | Morrison et al. | 106/212 |
| 4,323,694 | 4/1982 | Scala, Jr. | 514/846 |
| 4,397,913 | 8/1983 | Fahey | 106/212 |
| 5,207,827 | 5/1993 | Tokarz | 106/212 |

*Primary Examiner*—Anthony Green
*Attorney, Agent, or Firm*—John P. Halvonik

[57] ABSTRACT

The invention is an improved ear plug composition wherein the improvement comprises the use of cotton fibers as an additional ingredient in a natural ear plug composition comprising: wax, a starch based acid ester of dicarboxylic acid, lanolin, grapefruit seed extract as well as other vitamins, etc. The use of cotton fibers in an earplug composition adds strength to the composition and tends to maintain the ear plug in one homogeneous mass.

6 Claims, No Drawings

NATURAL EAR PLUG COMPOSITION

BACKGROUND AND PRIOR ART OF THE INVENTION

The invention is an improvement on applicant's previous ear plug composition, the subject of U.S. Pat. No. 5,207,827, which is hereby incorporated by reference. The improvement comprises the addition of cotton fiber and the substitution of lanolin for lecithin in the natural ear plug compositions described in the above referenced invention.

The applicant's ear plug compositions described in U.S. Pat. No. 5,207,827 have been improved through the use of cotton fiber to strengthen the ear plug composition and to maintain a homogeneous mass that will not break apart in the ear. Also that composition is improved through the use of lanolin in place of lecithin. It is believed that lanolin provides water repellancy to the composition for a longer time period than the lecithin. It is believed that using all natural ingredients in an earplug composition makes for a safer, biodegradable earplug.

SUMMARY OF THE INVENTION

The invention is an improved natural ear plug composition comprising: 1 part wax, 4 parts starch based acid ester of dicarboxylic acid, 1 part lanolin, a small amount of cotton fiber sufficient to add structural integrity to the composition and trace amounts of grapefruit seed extract (on the order of 0.05% by volume) and vitamins ( on the order of 0.25% by the volume for each). The cotton fiber is used in small proportions-about 0.6% by weight of the composition. The use of lanolin provides longer lasting water repellancy to the composition. The cotton fiber is added to the other ingredients of the composition while the composition is at an elevated temperature. After addition of the cotton fiber, the fiber is mixed into the composition and the composition is then cooled.

It is an object of the invention to provide an ear plug composition made of natural ingredients that has structural integrity so that it will not break apart when placed in the ear.

Another object is to provide an ear plug composition of natural ingredients that will remain tacky and elastic after prolonged use and after exposure to temperature extremes.

Another object is to provide an ear plug composition of natural ingredients that is biodegradable and non-toxic.

Other objectives of the invention will become apparent to those skilled in the art once the invention has been shown and described.

DESCRIPTION OF THE PREFERRED EMBODIMENT

The base ear plug composition are made of all natural ingredients and may be made by the process described in the applicant's prior U.S. patent application referred to above. In the compositions described herein, lanolin is substituted for the lecithin described in the prior U.S. patent. The additional ingredient of cotton fiber is used in these compositions. Such cotton fiber may be obtained from cotton balls, or other sources.

The preferred recipe calls for: 1 part lanolin, 1 part wax (yellow beeswax is preferred), and 4 parts modified starch (preferably a starch based ester of a dicarboxylic acid), and trace elements of vitamins and a biocidally effective amount of grapefruit seed extract in addition to the use of a small amount of cotton fiber. Cotton fiber in the preferred composition would comprise about 0.6%.

The wax, lanolin and starch are mixed together and raised to a temperature of about 140°–160° celsius, a small amount of cotton is added to the composition and the ingredients are mixed. The other ingredients such as vitamins (e.g. vitamins A, C, and E) and Grapefruit seed extract may be added at this time. The mixing may be done manually by using forks, etc. Other methods of mixing the composition are also possible. After the composition is cooled, it is then ready to be shaped into ear plugs.

It is believed that the use of the cotton fibers adds strength to the composition and enhances the ability of the ingredients to stay together as one mass, i.e. structural integrity of the ear plug mass is preserved. Without being bound by theory, it is believed that the cotton fibers intertwine with each other creating a network throughout the mass that lends stability to the mass.

This is important for ear plug compositions in the event that the ear plug composition is pushed very deep in the ear canal it is important to prevent the mass from breaking apart. Although inserting the composition deep into the ear is not recommended, the possibility remains that some people will insert the plug deep into the ear canal and risk breaking off portions of the plug. The use of cotton fibers minimizes the possibility that portions of the ear plug will break off.

The use of the lanolin enhances the earplug's ability to repel water, i.e. the surface is hydrophobic. This prevents water from soaking into the mass and causing it to deteriorate.

I claim:

1. A composition, especially useful for earplugs comprising: about 1 part by volume wax, 4 parts by volume starch based acid ester of a dicarboxylic acid, 1 part by volume lanolin and an amount of cotton fiber effectively able to make said composition structurally integral.

2. The composition of claim 1 in addition comprising a biocidally effective amount of grapefruit seed extract.

3. The composition of claim 2 in addition comprising 0.25% by volume of vitamin C.

4. The composition of claim 3 in addition comprising 0.25% by volume of vitamin E.

5. The composition of claim 1 in addition comprising 0.25% by volume of vitamin A.

6. The composition of claim 1 wherein said starch based ester is Aluminum Starch Octenylsuccinate.

* * * * *